(12) United States Patent
Solem

(10) Patent No.: US 6,179,848 B1
(45) Date of Patent: Jan. 30, 2001

(54) ANASTOMOTIC FITTING

(76) Inventor: Jan Otto Solem, Nordmannavägen 20, 237 31 Bjärred (SE)

(*) Notice: Under 35 U.S.C. 154(b), the term of this patent shall be extended for 0 days.

(21) Appl. No.: 09/228,749

(22) Filed: Jan. 12, 1999

Related U.S. Application Data

(63) Continuation of application No. PCT/SE97/01309, filed on Jul. 23, 1997.

(30) Foreign Application Priority Data

Jul. 24, 1996 (SE) .................................................. 9602849

(51) Int. Cl.⁷ .................................................. A61B 17/08
(52) U.S. Cl. ............................................................ 606/153
(58) Field of Search ........................... 606/153, 151–152, 606/154, 155, 198, 200; 623/1, 12; 604/8, 96, 101

(56) References Cited

U.S. PATENT DOCUMENTS

| | | |
|---|---|---|
| 2,453,056 | 11/1948 | Zack . |
| 3,868,956 * | 3/1975 | Alfidi et al. ................. 606/198 X |
| 4,233,981 * | 11/1980 | Schomacher ....................... 606/153 |
| 4,366,819 * | 1/1983 | Kaster ............................. 606/153 |
| 4,712,551 * | 12/1987 | Rayhanabad ..................... 606/153 |
| 4,787,386 | 11/1988 | Walsh et al. . |
| 5,309,894 * | 5/1994 | Heckele et al. ............. 606/153 X |
| 5,456,714 * | 10/1995 | Owen ................................ 623/1 |
| 5,695,504 * | 12/1997 | Gifford, III et al. ............ 606/153 |

FOREIGN PATENT DOCUMENTS

| | | |
|---|---|---|
| WO 93/00868 | 1/1993 | (WO) . |
| WO 95/17128 | 6/1995 | (WO) . |
| WO 97/43961 | 11/1997 | (WO) . |

\* cited by examiner

*Primary Examiner*—Michael H. Thaler
*Assistant Examiner*—Hoa B. Trinh
(74) *Attorney, Agent, or Firm*—Browdy and Neimark

(57) ABSTRACT

For connecting the end of a first blood vessel (6) to the side of a second blood vessel, the latter of which preferably has a greater diameter than the first blood vessel, an expandable end portion (12, 12') for forming an annular end flange (15, 15') is provided on a sleeve (11, 11'). As a result, the first blood vessel (6), after being passed through the sleeve (11, 11') in the direction of the expandable end portion and folding back at least over the expandable end portion, is formable into a collar, both sides of which enclose the annular end flange inside the second blood vessel and internally surround an opening formed therein.

19 Claims, 4 Drawing Sheets

ANASTOMOTIC FITTING

Figure 1:
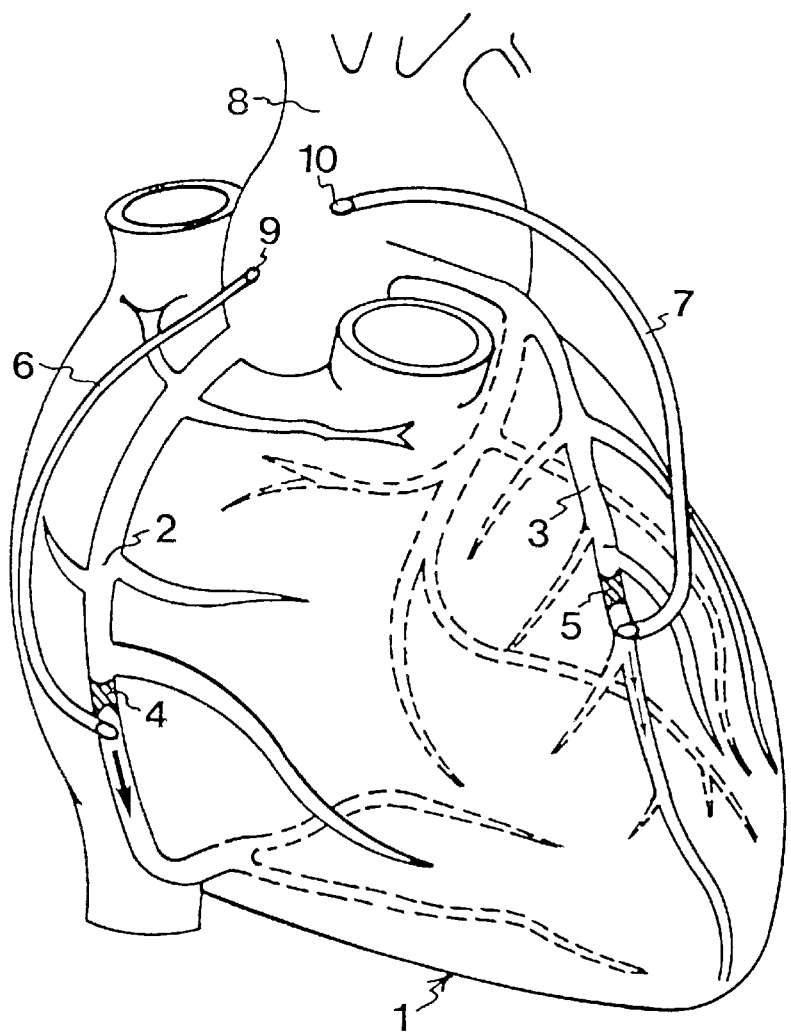

This application is a continuation of copending parent application Ser. No. PCT/SE97/01309, filed Jul. 23, 1997.

The present invention relates generally to the field of vascular surgery and, more specifically, to a connecting device for blood vessels, especially the aorta in by-pass operations on the coronary vessels.

An increased flow resistance in the various coronary vessels can jeopardise the oxygen supply to the cardiac muscle. In some cases an expansion of the vascular lumen is possible. If the flow of blood in a vessel is completely or practically completely blocked, the only thing to be done is to bypass the blocked portion to prevent an irreparable injury from arising. Such a bypass operation is usually effected by connecting a new vessel after the blocked point and connecting it to another blood vessel, for instance the aorta, which may give a sufficient flow of blood to the blood vessel after the blocked point.

Such a bypass operation normally requires the use of a heart-lung machine, i.e. that the heart be temporarily stopped, since the bypass operation when connecting, for instance, the two vessels involved requires the heart to be immovable. In consequence of the connecting technique employed and the use of the heart-lung machine, the operation will be relatively time-consuming and not without risk.

International Patent Application No. PCT/SE97/00804 discloses a branching device, which to a considerable extent facilitates the connection of the new vessel to the coronary vessel suffering from stenosis, but this branching device is not suited for connection of the new vessel to e.g. the aorta mainly owing to the difference in size.

The object of the present invention therefore is to provide a simple and reliable connection of the new vessel to a blood vessel, for instance the aorta, which can give a sufficient flow of blood to the constricted blood vessel via a branch after the constriction. Preferably it should also be possible to design the connection in a manner which makes it possible that the heart-lung machine need not be used. Most preferably it should be possible to carry out the operation by applying endoscopy.

According to the invention, this object is achieved by the connecting device being given the features that appear from the accompanying claim 1. Preferred embodiments of the connecting device appear from the dependent claims.

The inventive sleeve thus makes it possible to create a collar from the end of a first blood vessel. The collar can be made to extend around the inside of an opening formed in the second blood vessel. As a result, a relatively large overlapping can be achieved in the connecting area between the first and the second blood vessel, which in turn permits a highly reliable connection of the two vessels.

In the preferred embodiment, use is made of a balloon for expanding the end portion of the sleeve and, thus, for forming the collar. More precisely, the balloon is equipped with an inlet tube, which can be passed through the sleeve, such that the balloon itself will be positioned adjacent to the expandable end portion in order to accomplish, by inflation, the expansion thereof and at the same time also form the collar from the first blood vessel.

For fixing the position of the balloon during inflation thereof such that the resulting pressure acts against the expandable end portion of the sleeve, the inlet tube of the balloon suitably is made of a substantially nonelastic material.

In the preferred embodiment of the inventive device, the balloon besides has a nonelastic portion, which abuts on the inlet tube and in extended state has a shape corresponding to the desired shape of the annular end flange and, thus, the collar. This ensures still more that the expandable end portion of the sleeve is affected in the correct manner for the shape of the annular flange to be correct.

According to the invention, a locking ring is advantageously used to fix the two blood vessels. The locking ring can receive the sleeve and be displaced along this to a position adjacent to the annular flange, mutually overlapping portions of the first and the second vessel being positioned therebetween. With the aid of suitable fixing means, e.g. pins with barbs, which can be integrated with the locking ring and directed axially relative to the sleeve, the first and the second blood vessel portions, which overlap each other, can be interconnected in a simple and reliable manner around the opening formed in the second blood vessel.

The entire sleeve but preferably only its expandable end portion can advantageously be made of a net-like flexible material, but the end portion can alternatively be formed by making a plurality of axial slots from the one end of the sleeve.

Figure 5:
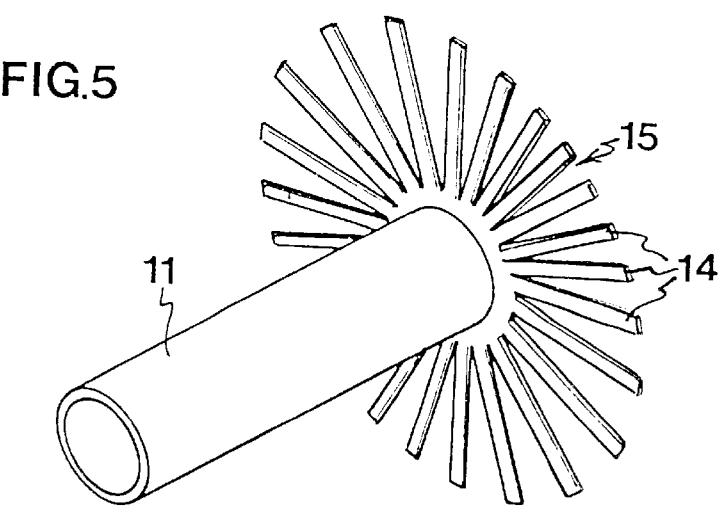
Figure 2:
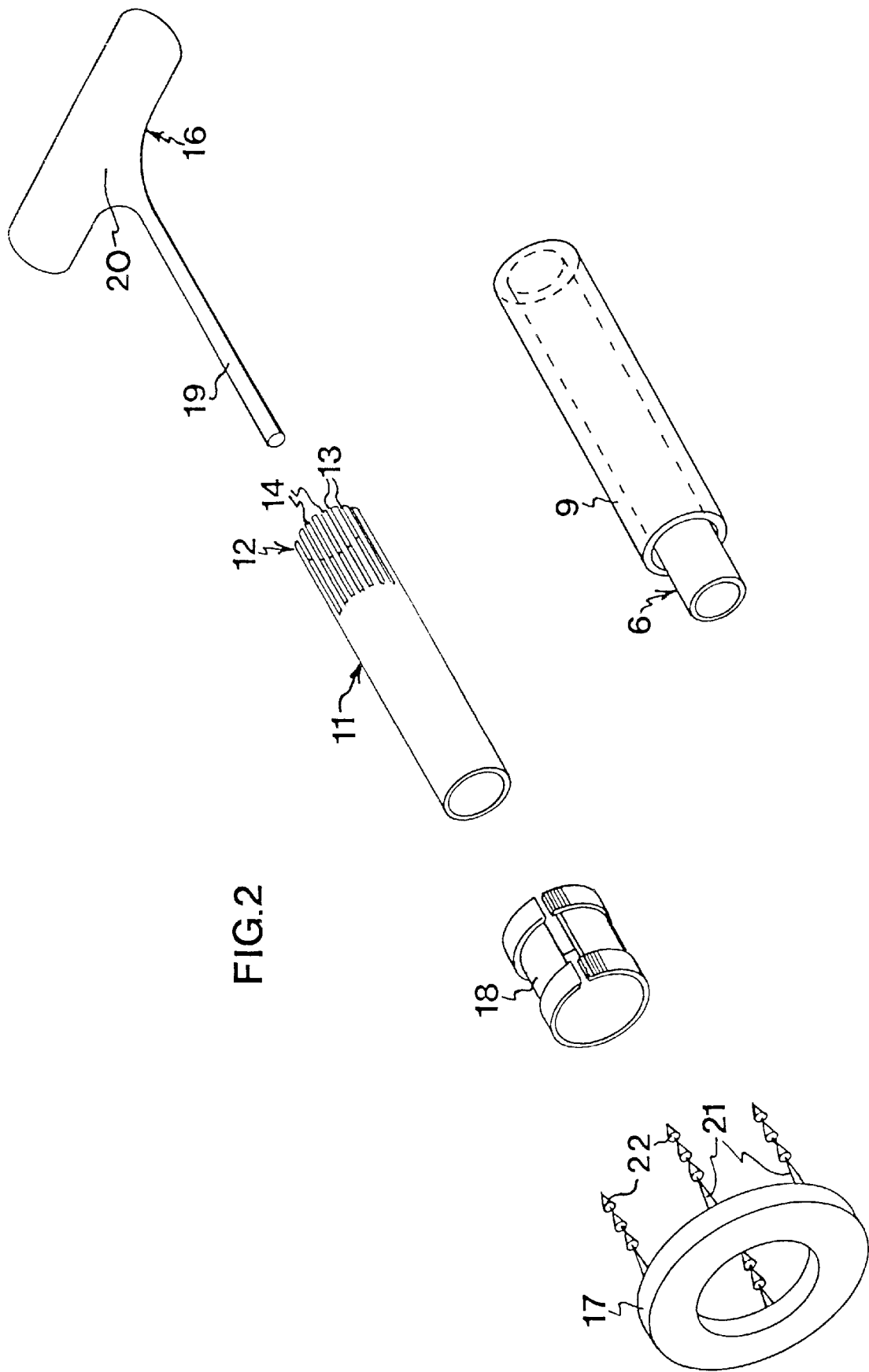
Figure 3:
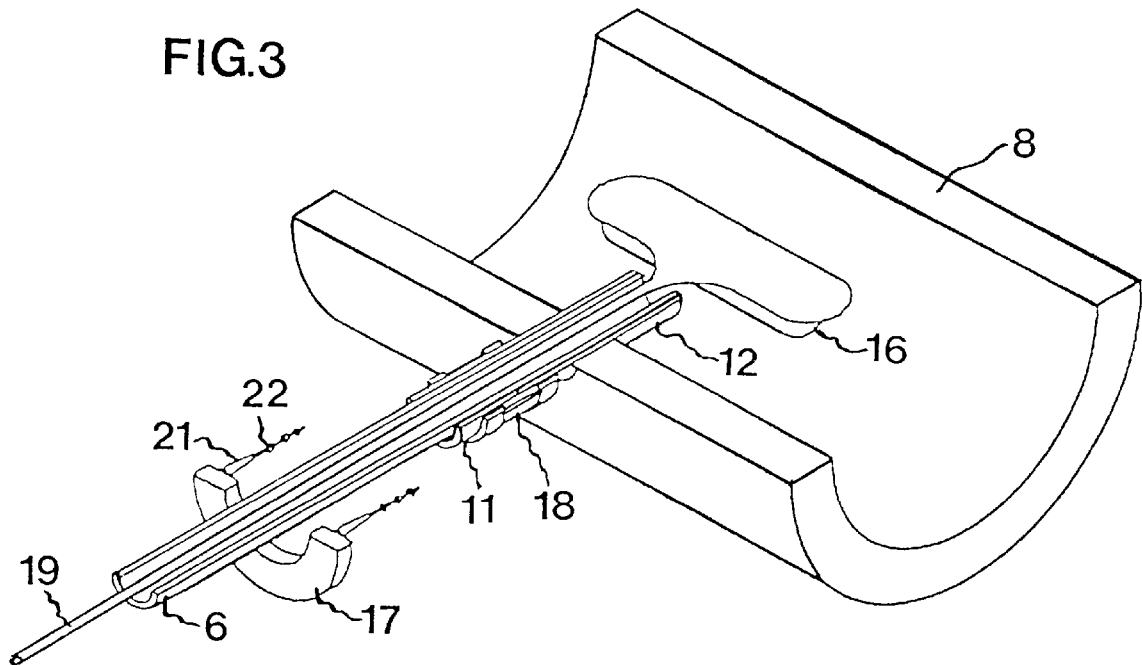
Figure 4:
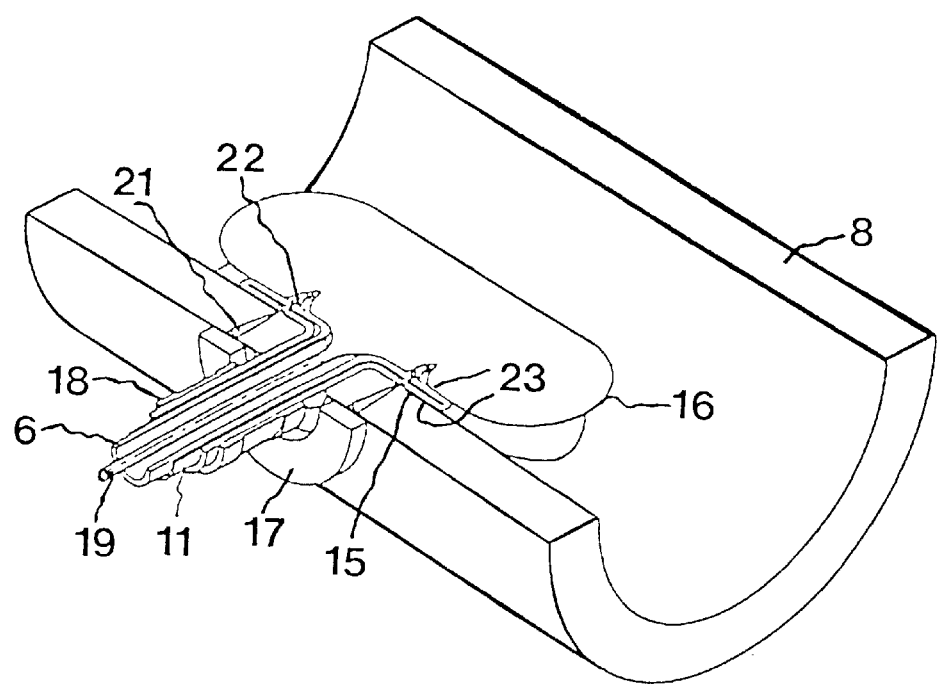
Figure 6A:
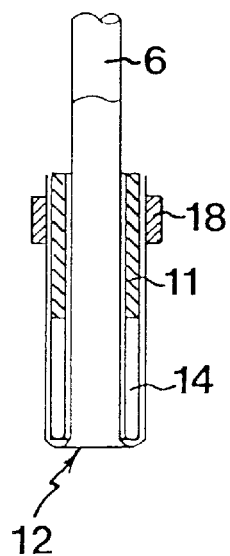
Figure 6B:
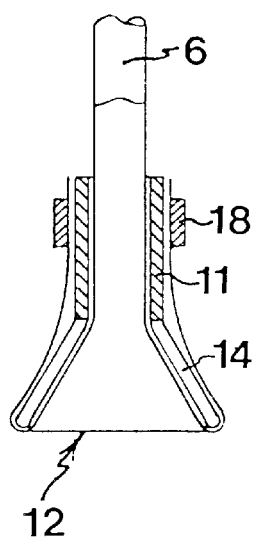
Figure 6C:
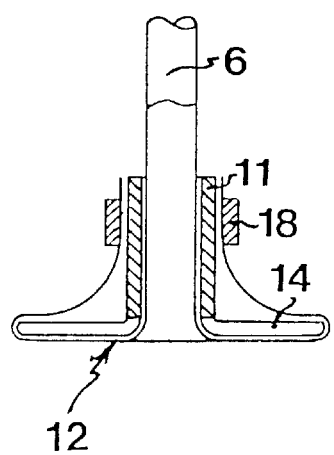
Figure 7:
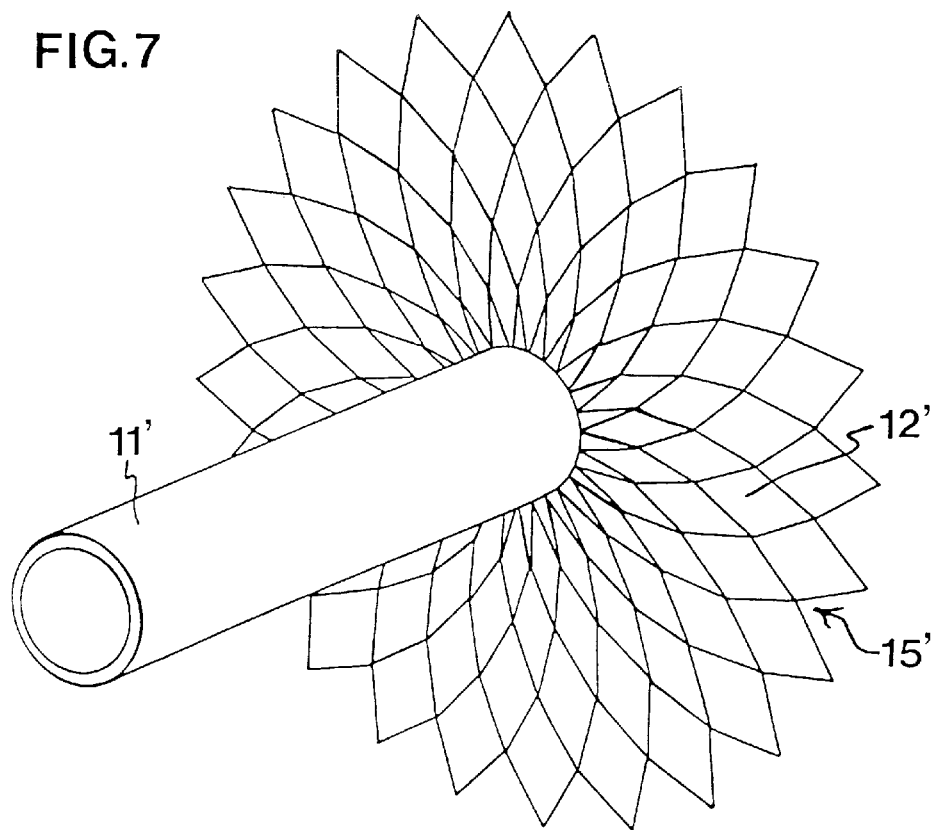

The invention will now be described in more detail with reference to the accompanying drawings, in which FIG. 1 is a perspective view and shows a heart with two schematically indicated bypasses of coronary vessels each having a blocking, FIG. 2 is a perspective view and shows one embodiment of a device according to the invention, as well as parts preferably associated therewith, FIGS. 3 and 4 are perspective views for explaining the method of mounting the embodiment of an inventive device as shown in FIG. 2, FIG. 5 is a perspective view of the inventive sleeve with an end portion expanded into an annular flange, FIGS. 6a–c illustrate schematically the procedure when forming a flange on the inventive sleeve when this is enclosed by a vessel, and FIG. 7 is a perspective view of an alternative embodiment of the sleeve in FIG. 5.

The heart 1 shown in FIG. 1 has two coronary vessels 2, 3 each having a blocking 4, 5 in the form of a stenosis or an occlusion. FIG. 1 illustrates schematically how these blockings are bypassed by means of two vessels 6, 7 which can be taken from the patient himself. More specifically, one end of the vessel 6 is connected after the blocking 4, seen in the normal direction of flow in the vessel 2, and its other end is connected to the aorta 8, such that a sufficient quantity of oxygen-rich blood will be supplied to the already blocked coronary vessel 2 after the blocking 4 therein. The same applies to the vessel 3.

For effecting the connection of the vessel 6 to the coronary vessel 2, a branching device according to International Patent Application No. PCT/SE97/00804 can be used.

The connecting device according to the present invention concerns the connection of the other end 9, 10 of the vessel 6 or 7 to a vessel, e.g. the aorta 8, which thus should give a sufficient flow of blood to provide the coronary vessel 2, 3 after the blocked point 4, 5 with a sufficient supply of oxygen.

As shown in FIG. 2, the connecting device according to the invention comprises a sleeve 11 of a metal or plastic that is not rejected by body tissue. The sleeve 11 comprises an end portion 12 having a plurality of axial slots 13 and axially directed, intermediate ribs 14. Except for the end portion 12, the sleeve 11 is relatively rigid. The ribs 14 of the end portion 12 are also relatively rigid, but flexible outwards from their axial direction in FIG. 2 to a radial direction, as is best seen in FIG. 5. In the outwardly-flexed state, the ribs 14 form an annular radial end flange 15, as is also best seen in FIG. 5.

An alternative to the sleeve 11 in FIG. 5 is shown in FIG. 7. Instead of having the slots 13 and the ribs 14, the sleeve 11' in FIG. 7 is, at least at its end 12', made of a net-like flexible material, e.g. of stent type, so as to give the flange 15' of the sleeve 11' the appearance which is schematically shown in FIG. 7.

The connecting device further utilises a balloon 16, a locking ring 17 and a locking sleeve 18. FIG. 2 also shows part of the first blood vessel 6 adjacent to the end 9 thereof. More precisely, the blood vessel 6 is shown in the form it gets after being passed, end 9 first, through the sleeve 11 in the direction of the end portion 12 of the sleeve and subsequently has been folded back with its outer part over the sleeve 11.

The balloon 16 is made of an elastic material, but has an inlet tube 19 which is essentially nonelastic. The inlet tube 19 is adapted to be passed through the vessel 6, for instance after the vessel 6 has been arranged on the sleeve 11 in the manner described above. The balloon may also comprise an essentially nonelastic portion 20 adjacent to the inlet tube 19 for a purpose that will be described below.

The locking ring 17 is an essentially planar ring having a plurality of axially directed pins 21, which project in the same direction from one flat side of the ring. Each pin 21 has one or more barbs 22, which ensure that the pin 21 remains once it has been passed through a material, in this case the vessel 6 and the end flange 15, as will be described in more detail below.

The locking sleeve 18 serves to safely retain on the sleeve 11 that part of the vessel 6 which has been folded back over the sleeve 11 and past the end portion 12. More specifically, the locking sleeve 18 is of such a design that it can be opened and be moved inwards laterally over that part of the vessel 6 which has been folded back over the sleeve 11, and then be clamped, such that the interiorly of the locking sleeve 18 positioned part of the vessel 6 is locked against the sleeve 11. Alternatively, the locking sleeve 18 can be integrally formed with the locking ring 17.

A method for connecting the vessel 6 to the vessel 8 by means of an inventive device will be described below with reference to FIGS. 3 and 4.

The end 9 of the vessel 6 is first passed through the sleeve 11 and folded back over the end portion 12 and somewhat past this. The folded-back part of the vessel 6 is fixed on the sleeve 11 by means of the locking sleeve 18. The inlet tube 19 of the balloon 16 is moved through the vessel 6, and the locking ring 17 is moved inwards over the vessel 6 from the end thereof which is opposite to the balloon 16.

After an opening has been made in the wall of the vessel 8, the sleeve 11 with the vessel 6 pulled over and locked by means of the locking ring 18 and with the balloon 16 positioned within the sleeve 11 is moved so far into the vessel 8 that the end portion 12 is positioned completely inside the vessel 8. The balloon 16 is then inflated via its inlet tube 19, the balloon 16 being in such a position that the ribs 14 are bent outwards from their axial direction to a more or less radial direction. This deformation of the end portion 12 is permanent, and thus the end flange 15 is formed. The fact that the inlet tube 19 is not elastic makes it easy for the balloon 16 to affect the ribs 14 in the correct manner for the desired outwards bending thereof. The desired shape of a collar 23 formed from the vessel 6 around the end flange 15, i.e. the shape of the end flange 15, can be additionally guaranteed by the balloon portion 20 adjacent to the inlet pipe 19 also being formed essentially nonelastic.

When inflating the balloon 16, the shape of the sleeve 11 changes from the shape shown in FIG. 3 to the one in FIG. 4 (and also FIG. 5).

The change of the shape is shown in more detail in FIGS. 6a–c, where the sleeve 11 and the first vessel 6 are shown in a longitudinal cross-section, but where the balloon 16 is not included for the sake of clarity.

FIG. 6a shows the starting position, where the first vessel 6 is passed through the sleeve 11 and is folded back practically to the end of the sleeve 11 opposite the end 12, and where the locking ring 18 fixes the folded-back part of the first vessel 6 adjacent to the former end.

FIG. 6b shows the position after the expansion of the end portion 12 of the sleeve 11 has begun. The first vessel 6 will, on the inside of the sleeve 11, essentially abut on the inside of the end portion 12, while on the outside of the sleeve 11 it will extend essentially straight between the locking ring 18 and the free end of the end portion 12. Since this free end is not fixed relative to the first vessel 6, a relative movement will be possible, which is a requirement to enable expansion of the first vessel 6 without being damaged to a considerable extent.

FIG. 6c shows the final position of the expansion of the end portion 12 of the sleeve 11. Also in this case, the first vessel 6 follows the inside of the end portion 12 but does not enter the angle between the sleeve 11 and the expanded end portion 12 on the outside of the sleeve 11. This clearance between the vessel 6 and the outside of the sleeve 11 adjacent to the expanded end portion is advantageous for the necessary seal against the second vessel 8 since a pressure will thus be exerted on the inside of the edge of the opening formed in the vessel 8.

For the final fixing of the vessel 6 to the vessel 8, the locking ring 17 is moved down on the outside of the sleeve 11 towards the end flange 15, while the pins 21 penetrate at least the wall of the vessel 8 and the wall of that part of the vessel 6 which is folded back over the end portion 12 and forms one layer of the collar 23. Because of the barbs 22, the desired locking is achieved. The pins 21 can advantageously also be made to penetrate the end flange 15 and the other layer of the collar 23 and outwards into contact with the balloon 16, which, however, is so yieldable as not to be punctured by the pins 21.

Once the vessel 6 is safely connected to the vessel 8, the pressure in the balloon 16 can finally be relieved, thereby making it possible to pull out the balloon through the vessel 6 by means of the inlet tube 19.

The expert realises that several modifications of the above-described embodiment of a connecting device are conceivable within the scope of the invention as defined in the appended claims. For example, the fan shape which the ribs 14 of the end flange 15 have according to FIG. 5 can also be achieved without the slots 13 by folding the material of the end portion 12 like a fan.

What is claimed is:

1. A device for connecting the end of a first blood vessel (6) to the side of a second blood vessel (8), comprising a sleeve (11, 11') having a first diameter and an expandable end portion (12, 12') of diameter substantially the same as said first diameter, said end portion being expandable to form an annular flange (15, 15') having an outer periphery diameter substantially greater than said first diameter, said annular flange being adapted to be enclosed by the end of the first blood vessel (6) for forming a collar (12) for connecting the second blood vessel (8) and a balloon, which is arranged adjacent to the expandable end portion (12, 12') and is adapted to expand the end portion and form the collar (23) during inflation of the balloon.

2. A device as claimed in claim 1, wherein the balloon (16) has an inlet tube (19) of an essentially nonelastic material.

3. A device as claimed in claim 1, wherein the balloon (16) has an essentially nonelastic portion (20), which abuts on the inlet tube (19) and in extended state has the shape which is desired for the collar (23).

4. A device as claimed in claim 1, wherein the end portion (12, 12') of the sleeve (11, 11') is made of a permanently deformable material.

5. A device as claimed in claim 1, further comprising a locking ring (17) having a greater inner diameter than the outer diameter of the sleeve (11, 11') and having axially directed fixing means (21), said locking means being adapted to fix the collar (23) to the inside of the wall of the second blood vessel (8).

6. A device as claimed in claim 5, wherein the fixing means (21) comprise pins provided with barbs (22).

7. A device as claimed in claim 1, for further comprising clamping means (18), firing part of the first blood vessel (6) to the outside of the sleeve (11, 11').

8. A device as claimed in claim 1, wherein the expandable end portion (12') of the sleeve (11') is made of a net material.

9. A device as claimed in claim 8, wherein the sleeve (11, 11') is made of one of a metallic material and some other flexible material.

10. A device as claimed in claim 1, wherein the expandable end portion (12, 12') of the sleeve (11, 11') is outwardly foldable in the form of a fan.

11. A device as claimed in claim 3, wherein the end portion (12, 12') of the sleeve (11, 11') is made of a permanently deformable material.

12. A device as claimed in claim 11, further comprising a locking ring (17) having a greater inner diameter than the outer diameter of the sleeve (11, 11') and having axially directed fixing means (21), said locking means being adapted to fix the collar (23) to the inside of the wall of the second blood vessel (8).

13. A device as claimed in claim 12, wherein the fixing means (21) comprise pins provided with barbs (22).

14. A device as claimed in claim 13, further comprising a clamp adapted to fix part of the first blood vessel (6) to the outside of the sleeve (11, 11').

15. A device as claimed in claim 14, wherein the expandable end portion (12') of the sleeve (11') is made of a net material.

16. A device as claimed in claim 15, wherein the sleeve (11, 11') is made of one of a metallic material and some other flexible material.

17. A device as claimed in claim 14, wherein the expandable end portion (12, 12') of the sleeve (11, 11') is outwardly foldable in the form of a fan.

18. A device for connecting the end of a first blood vessel to the side of a second blood vessel having a greater diameter than the first blood vessel, said device comprising:

an elongated sleeve having an expandable end portion formed of a plurality of ribs separated by slots extending in a substantially axial direction;

means for deforming said expandable end portion within the second blood vessel to form an annular end flange within the second blood vessel a balloon, which is arranged adjacent to the expandable end portion (12, 12') and is adapted to expand the end portion and form the collar (23) during inflation of the balloon; and locking structure to fix said sleeve relative to the wall of the second blood vessel.

19. A method for fixing an end of a first blood vessel to the side of a second and larger blood vessel using the device of claim 1, comprising passing the end of the first blood vessel through said sleeve and locking said sleeve about said first blood vessel;

moving the balloon and an inlet tube of the balloon through said first blood vessel;

after an opening has been made in the wall of the second blood vessel, inserting said sleeve and said first blood vessel, with the balloon positioned within the sleeve, so far into the second blood vessel that said expandable end portion of said sleeve is positioned completely inside the second blood vessel;

inflating the balloon to cause rotation of the end portion of the sleeve to expand said end portion and form said annular flange;

locking said sleeve in place on said second blood vessel; and deflating said balloon and withdrawing said deflated balloon from said first blood vessel.

* * * * *